United States Patent [19]

Leichnitz

[11] Patent Number: 4,748,930
[45] Date of Patent: Jun. 7, 1988

[54] COLORIMETRIC GAS DOSIMETER

[75] Inventor: Kurt Leichnitz, Gross Grönau, Fed. Rep. of Germany

[73] Assignee: Drägerwerk Aktiengesellschaft, Fed. Rep. of Germany

[21] Appl. No.: 17,000

[22] Filed: Feb. 19, 1987

Related U.S. Application Data

[63] Continuation of Ser. No. 806,687, Dec. 9, 1985, abandoned.

[30] Foreign Application Priority Data

Dec. 14, 1984 [DE] Fed. Rep. of Germany ....... 3445638

[51] Int. Cl.⁴ .................... G01D 21/00; G01N 31/22
[52] U.S. Cl. .................... 116/206; 422/58; 422/86; 436/3; 436/902
[58] Field of Search .............. 116/206; 422/58, 60, 422/86–88; 435/807; 436/2, 3, 902

[56] References Cited

U.S. PATENT DOCUMENTS

| | | | |
|---|---|---|---|
| 2,787,782 | 4/1957 | Rosenblum et al. | 116/206 |
| 3,482,944 | 12/1969 | Plantz et al. | 422/87 |
| 4,154,794 | 5/1979 | Clyne | 422/88 |
| 4,158,958 | 6/1979 | Braun | 422/88 |
| 4,258,000 | 3/1981 | Obermayer | 422/55 |
| 4,272,480 | 6/1981 | Stull et al. | 422/86 |
| 4,436,819 | 3/1984 | Manning | 422/87 |

FOREIGN PATENT DOCUMENTS 92101 10/1983 European Pat. Off. .......... 436/902

Primary Examiner—William A. Cuchlinski, Jr.
Assistant Examiner—W. Morris Worth
Attorney, Agent, or Firm—McGlew and Tuttle

[57] ABSTRACT

A device for indicating the presence of a gas includes a closed housing having an interior wall with a color indicator disk on one side wall and an opposite wall having an opening with an inflow pipe for the inflow of the gas to be detected. The interior of the housing forms a flat measuring chamber having the side wall with the detector disk of a size comparable to the length and diameter of the inflow pipe so as to form a diffusion area across which a mass transport of the gas to be detected takes place, that is, largely independent of air currents. The color indicated disk advantageously has a circular periphery and the inflow pipe is of cylindrical section and it is smaller than one-fifth the diameter of the measuring chamber having the disk. Advantageously, the length of the pipe section is less than the thickness of the measuring chamber. The inflow pipe section advantageously includes a portion of its length extending into the interior of the measuring chamber and a filter interlayer is located in the pipe section.

9 Claims, 1 Drawing Sheet

COLORIMETRIC GAS DOSIMETER

This is a continuation of application Ser. No. 806,687 filed Dec. 9, 1985, now abandoned.

BACKGROUND OF THE INVENTION

Field of the Invention

This invention relates, in general, to gas indicating devices and, in particular, to a new and useful colorimetric gas dosimeter which is adapted to be worn on a person for the detection of gas.

The invention concerns a colorimetric gas dosimeter, which contains a color indicator disc on one side wall in a box-shaped, flat measuring chamber, and in which the gas inlet lies in the side wall of the measuring chamber away from the color indicator disc.

Colorimetric gas dosimeters that can be worn, like radiation dosimeters, on the clothing of workers are known in several forms from the DE-GM No. 79 16 943, for example. A uniform deposition of the harmful substances to be detected on the surface of an indicator disc is desired in these devices. Independence from air currents at the gas inlet is provided by a damper layer located in the front, resulting in a gas exchange by diffusion. The harmful substance component diffuses through a quite central layer of flow in the measuring chamber onto the surface of the indicator layer, causing the color reaction.

Because of the attempted uniform deposition on the indicator layer, a multi-chambered device is used when a distinction is to be made between different volumes of the gaseous harmful substance to be measured, with each chamber having a different sensitivity due to changes in measuring with the same indicator layer. The user can recognize how strong his exposure to a given harmful substance was by checking the individual discolored indicator discs from the most sensitive to the least sensitive chamber.

SUMMARY OF THE INVENTION

The invention provides a colorimetric gas dosimeter which makes direct conclusions about the converted mass of gas to be measured, i.e. about the exposure of the user, possible from the size of a discolored area on a single indicator disc.

The characteristic of the invention is in the cylindrical shaped pipe section that forms the gas inlet and is located in the area of the side wall of the measuring chamber. The length and the inside diameter of the pipe section has dimensions so that the pipe section itself forms a diffusion area over which a mass transport of the gas to be detected occured. This is largely independent of air currents.

Consequently, an indicator disk on proper size must be provided, and the dimensions of the cylindrical pipe section must be chosen to promote a defined mass transport preferably in the direction towards the center of the color indicator disc, with the diffusion and thus the reaction layer spreading radially from the area of contact on the color indicator disc during continuous feeding of the gas to be detected, until the edge of the indicator disc is reached, and thereby the indicating area exhausted. The indication, i.e. the size of the color area which forms a rection zone on the color indicator disc, is a measure for the product of concentration and exposure time.

A preferred practical example includes a measuring chamber and a color indicator disc which have a circular periphery. The testing of a model of the invention has shown that it is advantageous to keep the diameter of the cylindrical pipe section smaller than one-fifth of the diameter of the measuring chamber and the length of the pipe below the thickness of the measuring chamber. For use, the gas dosimeter is worn with the cylindrical pipe section extending forward into the surrounding environment. Proper devices for fastening the dosimeter, e.g. in the form of a button loop, can be provided on the device.

An advantageous modification has a cylindrical pipe section extending in sections into the interior of the measuring chamber, which lengthens the diffusion section provided by the pipe section in the direction of the central area of the surface of the color indicator disc. This modification results in an improvement of the peripheral sharpness of the color spread on the color indicator disc in dependence on the diffusion behavior of the gas to be detected and on the composition of the color indicator.

A cylindrical pipe section is generally used open, i.e. without additional filter attachment, which results in an adequate diffusion rate and thus in a high rate of indication. But the insertion of an intermediate filter layer, for example, in the form of a moisture trap, may also be useful for special gaseous substances to be detected and indicator substances.

The color indicator or color indicator disc as used in this invention, may be of the type that allows detection without visually recognizable reaction zone, with the aid of additional scanning devices, for example a UV-light source.

Accordingly, it is an object of the invention to provide an improved device for detecting gas which includes a small enclosed housing having an interior wall with a color indicator thereon and an opposite wall with an inflow pipe. The inflow pipe being for the inflow of gas and being sized so as to be a small proportion of the size of the indicator wall and being centrally positioned in respect thereto so that the inflow pipe forms a diffusion area across which a mass transfer of the gas to be detected takes place. This is largely independent of air currents.

A further object of the invention is to provide an improved construction of gas detection device using a color indicator.

A further object of the invention is to provide an indicating device which is simple in design, rugged in construction and economical to manufacture.

GENERAL DESCRIPTION OF THE PREFERRED EMBODIMENTS

Figure 1:
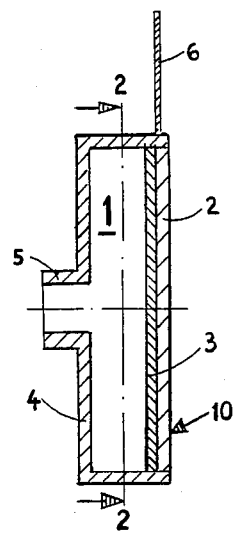
FIG. 1 is a longitudinal section of a colorimetric gas dosimeter ocnstructed in accordance with the invention.

Referring to the drawings, in particular, the invention embodied therein comprises a colorimetric gas dosimeter generally designated 10 which contains a color indicator disc 3 and a gas inlet 5 in the form of a cylindrical pipe section located approximately in the center of a front wall opposite the other back wall having the color indicator arranged within the measuring chamber defined by the housing.

This colorimetric gas dosimeter, which contains a color indicator disc in a flat measuring chamber, and in which the gas inlet lies on the side of the measuring chamber away from the color indicator disc, is improved for the continuous indication of a measuring value consisting of the product of the concentration and the duration of the exposure. This is achieved by providing the gas inlet in the shape of a cylindrical pipe section (5,8) that is located approximately in the center of the front wall area (4) of the measuring chamber (1), and keeping the length and the inside diameter of the pipe section (5,8) at such dimensions that the pipe section (5,8) forms a diffusion section over which a mass transport of the gas to be detected occurs largely independent of air currents (FIG. 1).

FIG. 1 shows a flat, box-shaped or disc-shaped housing 10 having a measuring chamber 1, which has a color indicator disc 3 attached to its back wall 2. A gas to be tested enters the axially symmetrical measuring chamber 1 through a coaxially located cylindrical pipe section 5, which has an inside diameter approximately one-eighth the inside diameter of the measuring chamber 1. The length of the pipe section 5 is less than the thickness of the open inside space of measuring chamber 1 between the back wall 2 and a front wall 4. A button loop 6 having a button hole 6a is provided for the fastening of the housing 10 to a person's clothing for example.

Figure 2:
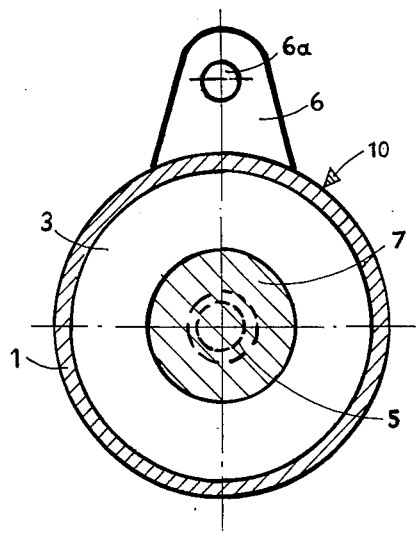
FIG. 2 is a cross-section taken along line 2—2 of FIG. 1.

FIG. 2 shows the measuring chamber housing 10 in cross-section and a reaction zone 7 in the shape of a circle is formed on the color indicator disc 3. FIG. 2 also shows the shape of the cylindrical side wall that bounds the sides of chamber 1.

Figure 3:
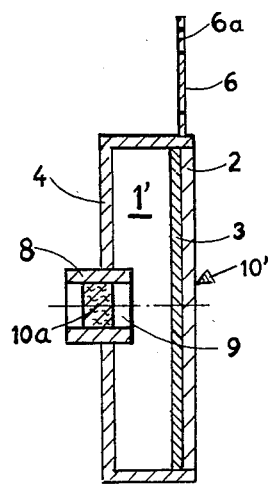
FIG. 3 is a view similar to FIG. 1 of an alternative practical embodiment of the invention.

In a practical embodiment according to FIG. 3, a color indicating gas dosimeter 10' includes a longer pipe section 8, which extends with its connection point 9 into the open inner space of a measuring chamber 1'. A moisture trapping filter interlayer 10a is located in pipe section 8. The other parts correspond to those of the embodiment according to FIG. 1.

While a specific embodiment of the invention has been shown and described in detail to illustrate the application of the principles of the invention, it will be understood that the invention may be embodied otherwise without departing from such principles.

What is claimed is:

1. A gas dosimeter comprising:
    a housing having a flat back wall with an inner surface, a flat front wall parallel to and spaced from said back wall, said front wall having an inner surface, and a side wall connected between said back and front walls, said side wall having an inner surface, said front, back and side walls together defining an enclosed measuring chamber for receiving a gas to be measured, said chamber having a thickness between said inner surfaces of said back and front walls which is small compared to a dimension of said chamber which is parallel to said front and back walls so that said chamber has a flat configuration;
    a color indicator disc capable of reacting with a gas and as a result thereof changing state which can be perceived, said disc being connected to said back wall engaged against said inner surface of said back wall; and
    an inlet pipe section connected to said front wall and extending out of said front wall, said pipe section having an inside and outside diameter, said front wall having an opening communicating with the exterior of said pipe section and having a diameter substantially equal to the outside diameter of said pipe section, the inside diameter of said pipe section being selected to be less than five times the dimension of said chamber extending parallel to said front and back walls, the length of said pipe section taken in a direction perpendicular to said front wall being selected to be less than the thickness of said chamber, said length of said pipe section being at least long enough to form a diffusion area so that a mass transport of gas entering into said chamber through said pipe section takes place so that said mass transport of gas is largely independent of air currents outside of said chamber, said pipe section being centrally located in said front wall, one portion of said inlet pipe sections extending out of said chamber and a second portion of said inlet pipe section extending into said chamber thereby directing the gas entering said chamber initially towards the center of said indicator disc, whereby the reaction takes place at a center of said indicator disc and propagates radially outwardly from the center of the indicator disc along the indicator.

2. A gas dosimeter according to claim 1, wherein said side wall of said chamber is cylindrical, said dimension of said chamber which is parallel to said front and back walls being the inside diameter of said side wall, said indicator disc being circular, said pipe section being cylindrical and said front and back walls being circular, said inlet pipe section being centered on centers of said front and back walls, a center of the inside diameter of said side wall and the center of said indicator disc.

3. A gas dosimeter according to claim 2, wherein said pipe section is entirely open for the free passage of gas.

4. A gas dosimeter according to claim 2, including a diffusion filter connected in and extending across the inside diameter of said pipe section.

5. A gas dosimeter according to claim 3, wherein said pipe section has a portion extending into said chamber and a portion extending out of said chamber.

6. A gas dosimeter according to claim 3, including a flat button loop fixed to said housing and extending substantially parallel to said front and back walls, said button loop having a button hole therein.

7. A gas dosimeter according to claim 4, including a flat button loop fixed to said housing and extending substantially parallel to said front and back walls, said button loop having a button hole therein.

8. A gas dosimeter according to claim 6, wherein said button loop is sbustantially coplanar with said back wall.

9. A gas dosimeter according to claim 7, wherein said button loop is substantially coplanar with said back wall.

* * * * *